United States Patent
Shaw et al.

(10) Patent No.: US 12,042,639 B2
(45) Date of Patent: Jul. 23, 2024

(54) MEDICAL SYRINGE WITH RETRACTABLE NEEDLE AND MODIFIED PLUNGER HANDLE WITH CONCAVE PRESSURE APPLICATION SURFACE

(71) Applicants: Retractable Technologies, Inc., Little Elm, TX (US); Thomas J. Shaw, Frisco, TX (US)

(72) Inventors: Thomas J. Shaw, Frisco, TX (US); Hannah Monique Myers, Little Elm, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 340 days.

(21) Appl. No.: 17/011,713

(22) Filed: Sep. 3, 2020

(65) Prior Publication Data

US 2022/0062558 A1 Mar. 3, 2022

(51) Int. Cl.
*A61M 5/32* (2006.01)
*A61M 5/31* (2006.01)
*A61M 5/315* (2006.01)

(52) U.S. Cl.
CPC ........ *A61M 5/3148* (2013.01); *A61M 5/3137* (2013.01); *A61M 5/31511* (2013.01); *A61M 5/322* (2013.01); *A61M 5/3295* (2013.01); *A61M 2005/3201* (2013.01); *A61M 2205/02* (2013.01)

(58) Field of Classification Search
CPC ............ A61M 5/3137; A61M 5/31511; A61M 5/322; A61M 2005/3241; A61M 2005/3231; A61M 2005/323; A61M 5/3148; A61M 2005/3123
See application file for complete search history.

(56) References Cited

U.S. PATENT DOCUMENTS

| | | | |
|---|---|---|---|
| 5,632,733 A | 5/1997 | Shaw | |
| 5,810,775 A | 9/1998 | Shaw | |
| 5,997,512 A | 12/1999 | Shaw | |
| 6,015,438 A | 1/2000 | Shaw | |
| 6,090,077 A | 7/2000 | Shaw | |
| 6,572,584 B1 | 6/2003 | Shaw et al. | |
| 7,351,224 B1 | 4/2008 | Shaw | |
| 2006/0223027 A1* | 10/2006 | Smith | A61C 5/62 433/90 |
| 2009/0182284 A1* | 7/2009 | Morgan | A61M 5/3202 604/227 |
| 2011/0230844 A1* | 9/2011 | Shaw | A61M 5/3234 604/198 |

* cited by examiner

*Primary Examiner* — James D Ponton
*Assistant Examiner* — Hong-Van N Trinh
(74) *Attorney, Agent, or Firm* — Scheef & Stone, LLP; Robin L. Barnes; Mike Schofield

(57) ABSTRACT

A medical syringe having a forwardly projecting needle that is selectively retractable following use and also having a specially configured plunger handle and thumb cap that cooperate to form a concave pressure application surface ("CPAS"). The concave pressure application surface at the rear of the plunger handle enables the subject medical syringe to achieve functional advantages, each with an associated therapeutic benefit, that are not achieved with use of the prior art devices.

20 Claims, 3 Drawing Sheets

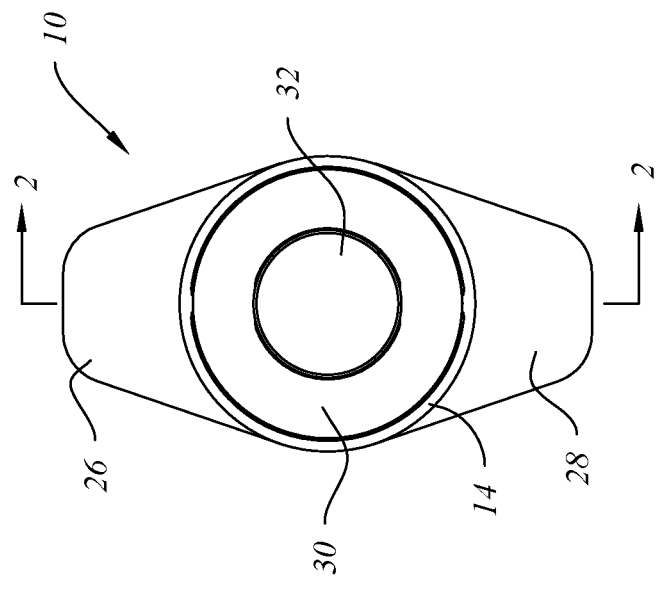
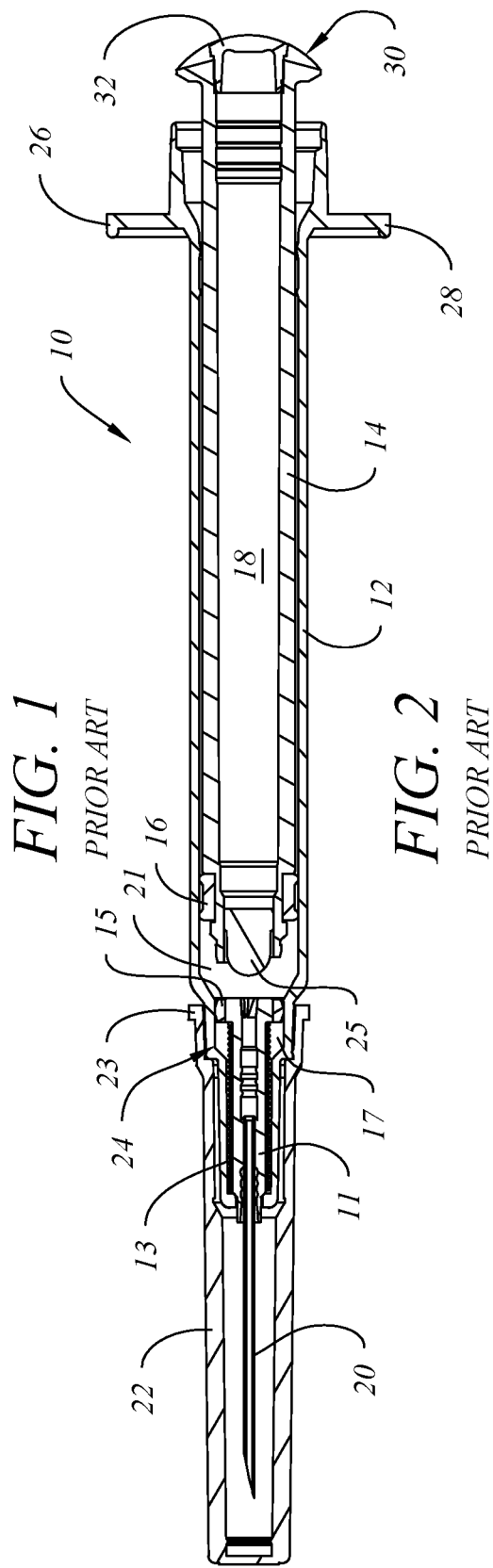
FIG. 1
PRIOR ART
FIG. 2
PRIOR ART

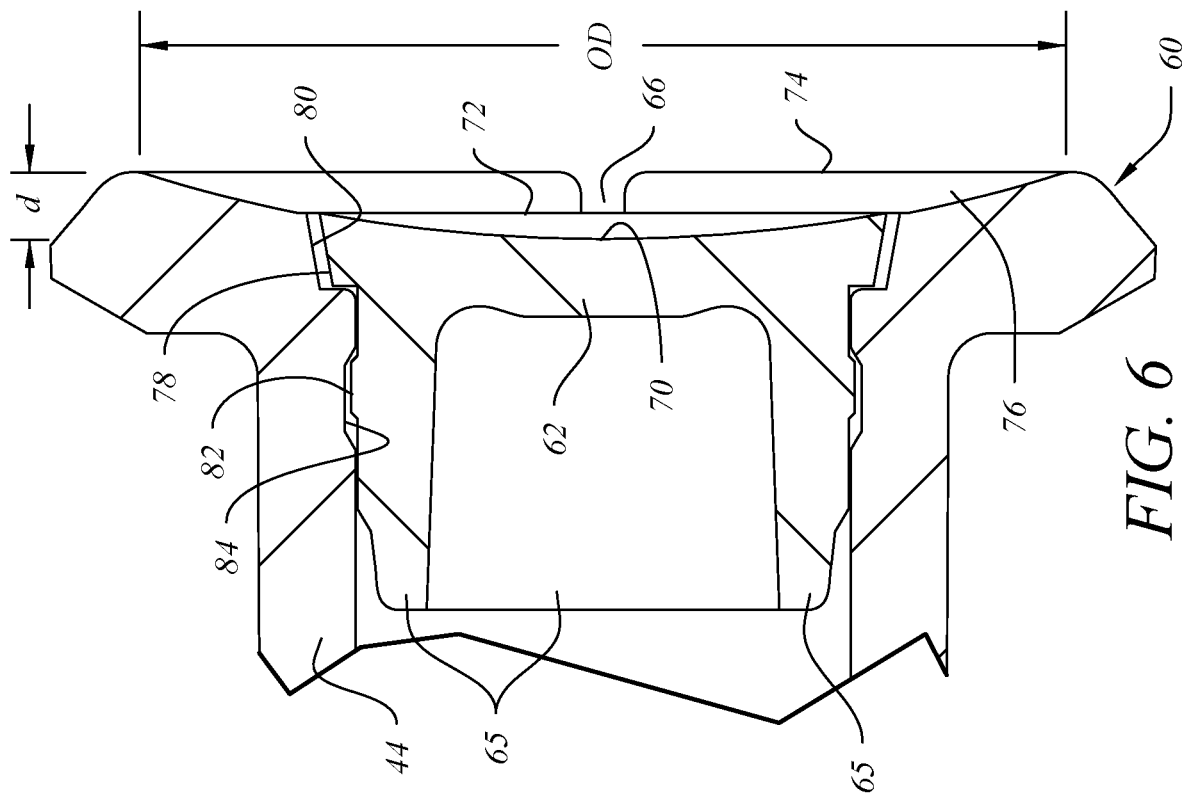
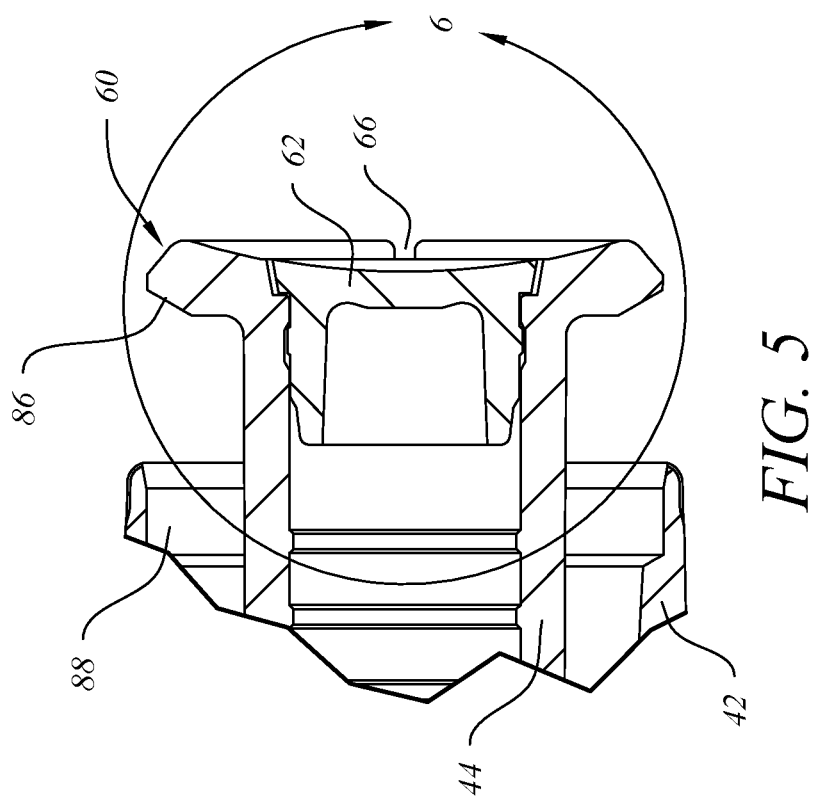

MEDICAL SYRINGE WITH RETRACTABLE NEEDLE AND MODIFIED PLUNGER HANDLE WITH CONCAVE PRESSURE APPLICATION SURFACE

1. FIELD OF THE INVENTION

This invention relates to a syringe for medical use and more particularly to a syringe having a plunger handle comprising a needle retraction cavity and a concave pressure application surface that enables a user to more easily, comfortably and safely administer an injection and to initiate needle retraction into the needle retraction cavity following the injection.

2. BACKGROUND ART

Syringes are previously known that comprise a barrel, a tubular plunger handle having a flexible seal slidably engaging an inside wall of the barrel and a forwardly projecting needle seated inside a nose portion of the barrel. In some such syringes, a forwardly projecting needle and a needle holder are biased rearwardly by a compressed spring and are restrained against the biasing force by an elastomeric friction ring disposed between the needle holder and an inside wall section of the barrel. In some such syringes, the needle is selectively retractable following use into a coaxially aligned needle retraction cavity disposed inside the plunger handle. As an injection is administered to a patient by continually depressing the thumb cap of the plunger handle while maintaining opposing pressure on the finger flanges of the barrel, the plunger tip contacts and pushes the friction ring forwardly off the head of the needle holder at the same time that the head of the needle holder contacts a plunger plug disposed inside a front opening of the plunger handle and pushes it rearwardly. As the friction ring is disengaged from the needle holder and the plunger plug is dislodged, the rearwardly biased needle and needle holder are driven rearwardly into a protected position inside the coaxially aligned needle retraction cavity. Desirably, as the compressed spring expands following release of the needle holder by the friction ring, the forwardly facing needle tip is withdrawn from the patient and into a protect position inside the syringe without risk of an accidental needle stick as might otherwise occur with a differently configured syringe. Following needle retraction, the needle tip is withdrawn at least inside the forward portion of barrel 12 to prevent accidental needle stick injuries of the type that might otherwise occur with a different syringe product. Syringes of the type described above are disclosed, for example, in U.S. Pat. Nos. 5,632,733; 5,810,775; 5,997,512; 6,015,438; 6,090,077; 6,572,584 and 7,351,224.

With prior art medical syringes such as those disclosed in the patents identified above, the proximal end of the plunger handle typically comprises a flat or convex "thumb cap" that flares radially outward around the rearwardly facing opening of the tubular section of the handle and has a perimeter with an outside diameter that is designed to abut against the proximal end of the sidewall of the syringe barrel or to seat or "nest" inside an annular recess disposed in the proximal end of the barrel to reduce the likelihood that the plunger handle will be withdrawn axially from the syringe barrel following needle retraction. The thumb cap portion of the plunger handle also typically comprises an inwardly facing aperture with an inside diameter that is tapered to receive an end plug (sometimes colored) that is inserted into the thumb cap of the plunger handle during assembly of the syringe to block rear access to the interior of the needle retraction cavity. The end plug is typically frictionally engageable with the aperture of the thumb cap and also has a convex end proximal surface as shown, for example, in FIGS. 1-3 of U.S. Pat. No. 6,572,584.

SUMMARY OF THE INVENTION

Unlike the syringes disclosed in the prior art, the apparatus disclosed here is a medical syringe having a forwardly projecting needle that is selectively retractable following use and also having a plunger handle with a specially configured thumb cap and end plug that cooperate to form a concave pressure application surface ("CPAS"). The concave pressure application surface at the rear of the plunger handle enables the subject medical syringe to achieve three functional advantages, each of which provides an associated therapeutic benefit, that is not achieved with use of the prior art devices.

A first functional advantage achieved when administering an injection with a syringe having a plunger handle provided with a concave pressure application surface of the present invention is it that a greater portion of the forwardly directed pressure ("thumb force") applied manually by the thumb of a user against the thumb cap and end plug of the plunger handle is concentrated and focused inwardly toward the longitudinal axis of the plunger handle. This improves utilization of the thumb force being applied through the plunger handle, the plunger seal and the distally located plunger plug to push fluid through the syringe barrel, the needle, and into a patient receiving the injection. The associated therapeutic benefit can be particularly pronounced or significant when the user is administering an injection of a relatively large dose of a fluid having a high viscosity as compared with other injectable fluids or medicines. The provision and use of a concave pressure application surface formed by the cooperatively disposed proximal ends of the plunger handle thumb cap and proximal end plug are also believed to contribute significantly to smooth and continuous advancement of the plunger handle through the syringe barrel during an injection.

Concomitantly, a second functional advantage achieved by use of a syringe having a plunger handle provided with a concave pressure application surface of the invention is that no significant portion of the thumb force exerted by a user while administering an injection will be diminished, misdirected or misapplied as it can be if the user's thumb slips off the side of, or is not fully engaging, the available surface area as can occur if the pressure application surface is flat or convex rather than concave. An associated therapeutic benefit is also realized because any sideways movement or jerking caused by slippage of a user's thumb while applying pressure to the proximal end of the plunger handle can produce even greater movement of the needle tip inside a patient, thereby intensifying the discomfort experienced by the patient during an injection.

A third functional advantage achieved by use of syringe having a plunger handle provided with a concave pressure application surface is that the CPAS more comfortably conforms to the thumb of the user. By contrast, when a user applies thumb force against a convex proximal end of the plunger handle while opposing resistance pressure is applied against the finger flanges of the plunger barrel during an injection, the user is more likely to experience discomfort due to being "poked" by the proximal end of the plunger handle and, in response to the associated discomfort, may reduce the magnitude of the thumb force being applied to the proximal end of the plunger handle. Such a reduction in the applied thumb force can prolong the injection and lengthen the period of discomfort to both user and patient.

Although the accompanying drawings are not drawn to scale, it should be appreciated by those skilled in the art upon reading the detailed disclosure with reference to FIGS. 3-6 of the drawings that the depth of the CPAS as measured along the longitudinal axis of the syringe and the diameter of the CPAS as measured across the rearwardly extending edge of the plunger handle thumb cap can vary in accordance with nominal size (as expressed in mL of volume, such as a 3 mL) of the syringe and the diameter of the plunger handle. Applicants presently believe that the benefits of the invention are satisfactorily achieved when the ratio of the maximum depth of the concave portion of the cooperatively configured and assembled plunger handle (with the end plug installed inside the thumb cap) to the diameter of the inside aperture of the thumb cap at the widest portion of the CPAS ranges between about 0.06 and about 0.085, with a preferred ratio being about 0.078.

BRIEF DESCRIPTION OF THE DRAWINGS

The system and method of the invention are further described and explained in relation to the following drawings wherein:

FIG. 1 is a rear elevation view illustrative of a Prior Art medical syringe embodying some structural elements common to the present invention but having a plunger handle with a conventional thumb cap that does not embody the structural improvements of the present invention;

FIG. 2 is a cross-sectional, side elevation view of the Prior Art syringe of FIG. 1 taken along line 2-2 of FIG. 1;

FIG. 5 is an enlarged detail view, partially broken away, taken from FIG. 4;

and

FIG. 6 is an enlarged detail view, partially broken away, taken from FIG. 5.

Figure 3:
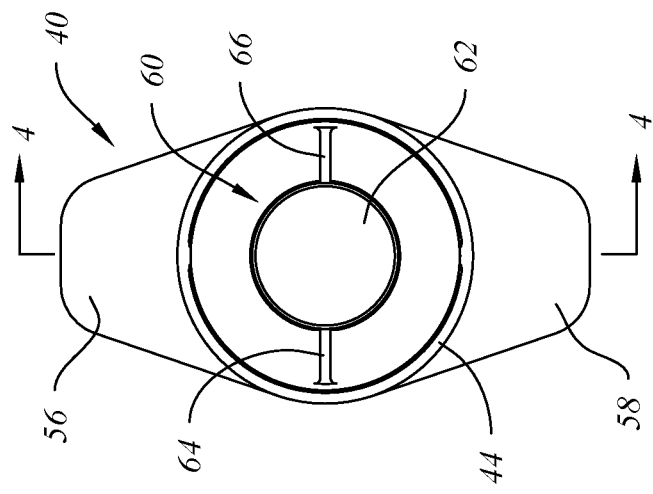
FIG. 3 is a rear elevation view of a preferred embodiment of the medical syringe of the invention.
Figure 4:
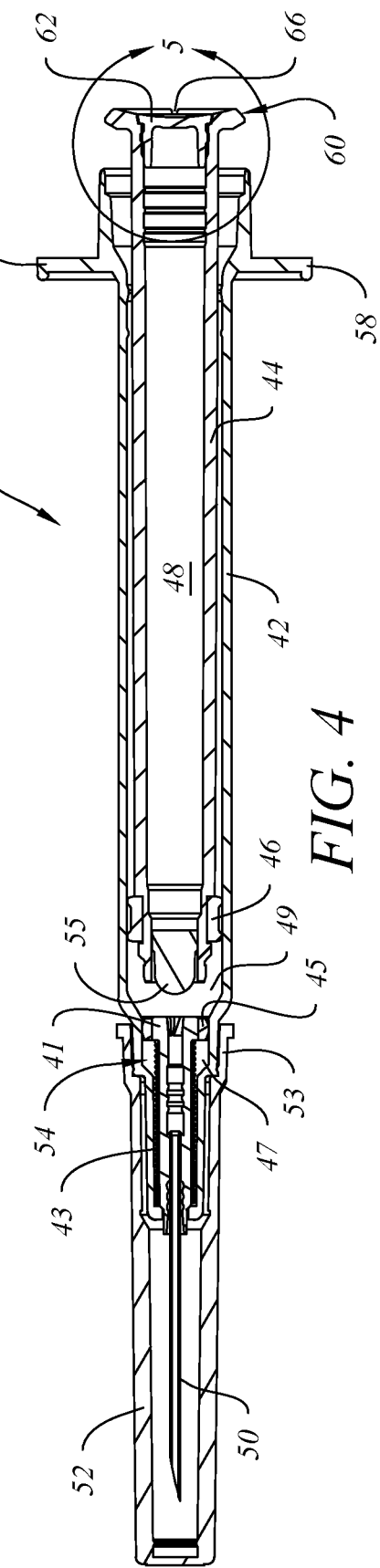
FIG. 4 is a longitudinal cross-sectional view of the medical syringe of FIG. 3 taken along line 4-4 of FIG. 3.

FIGS. 3-6 of the drawings are considered to be illustrative of the structural elements of the invention but are not drawn to scale.

DETAILED DESCRIPTION

FIGS. 1 and 2 depict prior art medical syringe 10 having some elements common to medical syringe 40 of the invention as is further described below in relation to FIGS. 3-6 of the drawings. Referring to FIGS. 1, 2, medical syringe 10 comprises cylindrical barrel 12 having a plurality of sections with differing inside diameters. Needle cap 22 comprises a proximal end with a collar portion 23 that frictionally engages an outwardly facing surface section of syringe barrel 12. A retractable needle assembly 24 comprising a needle holder 11 and a distally projecting needle 20 is seated inside a front portion of cylindrical barrel 12. Needle holder 11 and needle 20 are biased rearwardly by a coil spring 13 that is held in compression prior to and during an injection by a friction ring 15 or other similarly effective retainer member disposed between the needle holder 11 and an inside wall section of barrel 12. An elongate tubular plunger handle 14 comprising a centrally disposed needle retraction cavity 18 is inserted into cylindrical barrel 12 through a rearwardly facing opening disposed rearwardly of diametrically opposed, radially extending finger flanges 26, 28 of barrel 12.

The distal portion of plunger handle 14 further comprises an annular, elastomeric plunger seal 16 that slidably engages the inside wall of cylindrical barrel 12 and cooperates with a plunger plug 25 at the distal end of plunger handle 18 to define a variable volume fluid chamber 21 inside barrel 12 between retractable needle assembly 24 and plunger handle 14.

During use of prior art medical syringe 10, following the removal of needle cap 22, an injectable medication is typically aspirated into variable volume fluid chamber 21 disposed inside barrel 12 between retractable needle assembly 24 and plunger handle 14. After needle 20 is inserted into a patient, an injection is administered by advancing plunger handle 14 inside barrel 12 until plunger plug 25 contacts needle holder 11 of retractable needle assembly 24 and the injection is completed. Plunger handle 14 is typically advanced distally inside barrel 12 during an injection by applying thumb pressure forwardly against convex end surface 32 of thumb cap 30 of plunger handle 14 while simultaneously exerting opposed finger pressure rearwardly against the distally facing surfaces of opposed, outwardly projecting finger flanges 26, 28 of barrel 12. As the injection is completed, the continued thumb pressure exerted by the user against convex end surface 32 of thumb cap 30 of plunger handle 14 causes plunger plug 25 to contact the proximal end of needle holder 11, thereby dislodging plunger plug 25 from the distally facing opening of plunger handle 14. Simultaneously, the distal end of plunger handle 14 pushes friction ring 15 forwardly off the outer surface of needle holder 11 into annular space 17, allowing the compressed spring 13 to expand and drive needle holder 11 and plunger plug 25 rearwardly into needle retraction chamber 18. As needle holder 11 is driven rearwardly by the force of the expanding compressed spring, needle 20 is simultaneously withdrawn from the injection site of the patient and is carried rearwardly by needle holder 11. Following needle retraction, the needle tip is withdrawn at least inside the forward portion of barrel 12 to prevent accidental needle stick injuries of the type that might otherwise occur with a different syringe product.

Applicants have now discovered that a medical syringe of the type disclosed above can be further improved and provided with enhanced functionality by modifying the plunger handle to give the user greater comfort and control over injections and needle retraction, and to provide for smoother delivery of medications during an injection and for smoother needle retraction subsequent to the injection. A medical syringe having a plunger handle modified in accordance with the present invention is also particularly effective for use with highly viscous medications.

Referring now to FIGS. 3-6, medical syringe 40 of the invention comprises barrel 42, with elongate tubular plunger handle 44 slidably engaging an inside wall of barrel 42, elastomeric plunger seal 46, and retractable needle assembly 54 seated inside a front portion of barrel 42. Needle 50 is attached to and projects forwardly from needle holder 41 and is covered prior to use by removable needle cap 52 having a collar 53 at its proximal end that frictionally engages an outwardly facing wall portion near the front of barrel 42. Needle holder 41 and needle 50 are biased rearwardly by coiled spring 43 that is held in compression during an injection by a friction ring 45 disposed between needle holder 41 and an inside wall section of barrel 42.

Elongate tubular plunger handle 44 is desirably inserted into cylindrical barrel 42 through a rearwardly facing opening having an annular recess 88 with an inside diameter and depth sufficient to receive outermost portion 86 thumb cap 60 into nesting engagement inside recess 88 when plunger handle 44 is fully advanced inside barrel 42 and needle 50 is retracted following an injection. Such nesting engagement is desirable to deter possible reuse of a syringe for safety reasons and to deter the removal of plunger handle 44 from barrel 42 following needle retraction to reduce the likelihood of accidental needle sticks or inadvertent pathogenic contamination by contact with blood or other bodily fluids. The distal portion of plunger handle 44 further comprises an annular, elastomeric plunger seal 46 that slidably engages the inside wall of cylindrical barrel 42 and cooperates with plunger plug 55 at the distal end of plunger handle 44 to define a variable volume fluid chamber 49 inside barrel 42 between retractable needle assembly 54 and plunger handle 44. Each of the foregoing portions of medical syringe 40 except elongate tubular plunger handle 44 is configured and operates in substantially the same manner as described above in relation to the like portions of prior art medical syringe 10.

Referring now to the portion of plunger handle 44 disposed rearwardly of flange members 56, 58 of barrel 42 as viewed in FIGS. 3-6, a rearwardly facing, concave pressure application surface (CPAS) is formed at the rearwardly facing end of plunger handle 44 by the combined alignment of cooperatively configured thumb cap 60 and frictionally engaged end plug 62. Barrel 42, plunger handle 44, thumb cap 60 and end plug 62 of syringe 40 are all desirably made of a moldable thermoplastic material.

Referring more particularly to FIG. 6, the rearwardly facing end surface of end plug 62 is concave in shape, with a center point 70 marking the most forwardly extending point of the concave end surface and having a circumferentially extending outside edge 72 marking the most rearwardly extending portion of the concave end surface of end plug 62. Significantly, the concave proximal end surface of end plug 62 is disposed in juxtaposition to and is cooperatively aligned with and abuts a cooperatively curved, inwardly facing concave surface 76 of thumb cap 60 that extends rearwardly from outside edge 72 of end plug 62 to circumferentially extending rear edge 74 of thumb cap 60. The cooperatively configured and aligned portions of end plug 62 and thumb cap 60 thereby form a CPAS having a depth "d" representing the longitudinal distance between lowermost point 70 of end plug 62 and a diameter "OD" equivalent to the diameter of the circumferentially extending rear edge 74 of thumb cap 60.

As previously stated above, those skilled in the art will appreciate upon reading this disclosure with reference to FIGS. 3-6 of the drawings that the depth of the CPAS as measured along the longitudinal axis of syringe 40 and the OD of the CPAS as measured across the circumferentially extending rear edge 74 of thumb cap 60 can vary in accordance with nominal size (as expressed in mL of volume, such as a 3 mL) of the syringe and the diameter of the plunger handle. Applicants presently believe that the benefits of the invention are satisfactorily achieved when the ratio of the maximum depth "d" of the concave portion of the cooperatively configured and assembled plunger handle 44 (with end plug 62 installed inside the thumb cap 60) to the diameter "OD" of the inside aperture of the thumb cap at the widest portion of the CPAS ranges between about 0.06 and about 0.085, with a preferred ratio being about 0.078. This dimensional ratio is believed to provide a concave pressure application surface that will satisfactorily and comfortably focus the thumb force applied by a user to the rear of plunger handle 44 during an injection without significant risk of sideways slippage of the thumb on thumb cap 60 or discomfort to the user or patient as could otherwise occur. Further, use of syringe 40 with a concave pressure application surface (CPAS) formed by the cooperatively configured and aligned thumb cap 60 and end plug 62 will facilitate the injection of high viscosity medicines or other fluids while reducing discomfort to the user and patient.

End plug 62 desirably further comprises an inwardly tapered, forwardly extending skirt portion 65 that is inserted into and is sized to be frictionally engageable with at least a portion of the stepped inside wall defining tubular bore of plunger handle 44. Outwardly projecting annular protrusions 78, 82 on the outside of skirt portion 65 of end plug 62 loosely engage cooperatively aligned recesses 80, 84 to allow venting of air around end plug 62 from inside the tubular bore during needle retraction following an injection. Referring again to FIGS. 3-6, channels 64, 66 are provided in thumb cap 60 of syringe 40 to cooperate with aligned recesses 80, 84 to facilitate such venting even as thumb pressure is still being applied to the CPAS of plunger handle 44.

Other modifications and alterations to the apparatus disclosed here may become apparent to those of ordinary skill in the art upon reading this disclosure in relation to the accompanying drawings and it is intended that the scope of the invention disclosed herein be limited only by the broadest interpretation of the appended claims to which the inventors are legally entitled.

What is claimed is:

1. A medical syringe comprising:
   a barrel;
   a rearwardly biased, selectively retractable needle assembly coupled to the barrel and comprising a forwardly projecting needle; and
   a plunger slidably engaging an inside cylindrical wall of the barrel and comprising a plunger handle, a thumb cap and an end plug, the thumb cap and the end plug cooperating to form a rearwardly facing concave pressure application surface (CPAS) against which a forwardly directed thumb force is applied by a user, wherein the end plug comprises one or more outwardly projecting annular protrusions that loosely engage with one or more cooperatively aligned recesses on an inner wall of the thumb cap to allow venting of air around the end plug from an inside of the barrel when the plunger handle is fully advanced inside the barrel and the needle assembly is retracted within the barrel.

2. The medical syringe of claim 1, wherein the end plug has a concave proximal end surface disposed in juxtaposition to and cooperatively aligned with and abutting a cooperatively curved, inwardly facing concave surface of the thumb cap.

3. The medical syringe of claim 2, wherein the cooperatively curved, inwardly facing concave surface of the thumb cap extends rearwardly from an outside edge of the end plug to a circumferentially extending rear edge of the thumb cap.

4. The medical syringe of claim 1, wherein the CPAS is coaxially aligned with the plunger handle and has a depth-to-diameter ratio ranging from about 0.06 to about 0.085.

5. The medical syringe of claim 4, wherein the depth-to-diameter ratio is about 0.078.

6. The medical syringe of claim 1, wherein the plunger handle and the thumb cap are integrally molded from a thermoplastic resin.

7. The medical syringe of claim 1, wherein the end plug is molded from a thermoplastic resin and frictionally engages a rearwardly facing aperture in the thumb cap.

8. The medical syringe of claim 1, wherein the plunger handle is vented to release pressurized air between the thumb cap and the end plug when the plunger handle is fully advanced inside the barrel and the needle assembly is retracted within the barrel.

9. The medical syringe of claim 8, wherein the thumb cap is nestable inside a rearwardly facing opening of the barrel when the plunger handle is fully advanced inside the barrel.

10. The medical syringe of claim 1, wherein a portion of the barrel extends rearwardly from one or more finger flange members.

11. The medical syringe of claim 10, wherein an annular recess is formed in the portion of the barrel, and wherein the annular recess comprises an inside diameter and depth sufficient to receive an outermost portion of the thumb cap into a nesting engagement when the plunger handle is fully advanced inside the barrel.

12. The medical syringe of claim 11, wherein the nesting engagement prevents removal of the plunger handle from the barrel when the needle assembly is retracted within the barrel.

13. The medical syringe of claim 1, wherein the end plug comprises a skirt portion comprising the one or more outwardly projecting annular protrusions.

14. The medical syringe of claim 13, wherein channels formed in the thumb cap further facilitate the venting of air around the end plug from an inside of the barrel.

15. The medical syringe of claim 1, wherein the barrel is molded from a thermoplastic resin.

16. A method for administering an injection, comprising:
providing a medical syringe having a barrel, a rearwardly biased, selectively retractable needle assembly coupled to the barrel and comprising a forwardly projecting needle, and a rearwardly facing concave pressure application surface (CPAS) against which a forwardly directed thumb force is applied by a user a rearwardly facing concave pressure application surface (CPAS) against which a forwardly directed thumb force can be applied by a user, wherein the end plug comprises one or more outwardly projecting annular protrusions that loosely engage with one or more cooperatively aligned recesses on an inner wall of the thumb cap to allow venting of air around the end plug from an inside of the barrel when the plunger handle is fully advanced inside the barrel and the needle assembly is retracted within the barrel; and
thereafter applying a forwardly directed thumb force to the CPAS while administering the injection.

17. The method of claim 16, wherein the forwardly directed thumb force is applied to the CPAS while administering the injection of fluid characterized as having a "high viscosity".

18. The method of claim 16, further comprising, venting pressurized air between the thumb cap and the end plug when the plunger handle is advanced inside the barrel.

19. The method of claim 16, further comprising: venting pressurized air between the thumb cap and the end plug when the needle assembly is retracted inside the barrel.

20. The method of claim 16, wherein the CPAS is coaxially aligned with the plunger handle and has a depth-to-diameter ratio ranging from about 0.06 to about 0.085.

* * * * *